(12) United States Patent
Ndife et al.

(10) Patent No.: US 7,070,825 B2
(45) Date of Patent: Jul. 4, 2006

(54) INFANT FORMULA

(75) Inventors: Louis I. Ndife, Columbus, OH (US); Booker T. Lucas, III, Columbus, OH (US); Stephene L. Hohman, Worthington, OH (US)

(73) Assignee: Abbott Laboratories, Abbott Park, IL (US)

( * ) Notice: Subject to any disclaimer, the term of this patent is extended or adjusted under 35 U.S.C. 154(b) by 323 days.

(21) Appl. No.: 10/603,464

(22) Filed: Jun. 25, 2003

(65) Prior Publication Data

US 2004/0101596 A1 May 27, 2004

Related U.S. Application Data

(60) Provisional application No. 60/409,431, filed on Sep. 10, 2002.

(51) Int. Cl.
*A23C 9/18* (2006.01)

(52) U.S. Cl. .................. 426/580; 426/512; 426/601; 426/656; 426/658; 426/801; 426/468

(58) Field of Classification Search ................ 426/801, 426/512, 468, 580, 656, 601, 658
See application file for complete search history.

(56) References Cited

U.S. PATENT DOCUMENTS 3,241,975 A    3/1966    Brochner

FOREIGN PATENT DOCUMENTS

| DE | 4342124 | 6/1995 |
|---|---|---|
| EP | 0665012 | 2/1995 |
| GB | 894001 | 4/1962 |
| WO | WO9303633 | 3/1993 |
| WO | WO0156406 | 8/2001 |
| WO | WO02062152 | 8/2002 |
| WO | WO03077664 | 9/2003 |

OTHER PUBLICATIONS

Windholz, M. The Merck Index, 10$^{th}$ Ed. Merck 7 Co., Rahway, N. J., 1983, p. MISC-87.*

* cited by examiner

*Primary Examiner*—Helen Pratt
(74) *Attorney, Agent, or Firm*—William J. Winter

(57) ABSTRACT

The present invention is directed to a new unit dose packaging for infant formula. The infant formula is manufactured as a tablet. One tablet will typically contain sufficient nutrients to produce a single serving of the formula (i.e. the amount of formula an average infant consumes in a single feeding). Other aspects of the invention are directed to feeding an infant such a reconstituted tablet and packaging containing such infant formula tablets.

12 Claims, No Drawings

INFANT FORMULA

This application claims the benefit of Provisional Application No. 60/409,431, filed September.

The present invention is directed to a new means of providing a single serving of infant formula. The infant formula is compressed into tablets, which are subsequently dissolved prior to administration to the infant.

BACKGROUND

Tablets have been well known in the pharmaceutical industry since the late 19th century. Typically, a drug is mixed with inert ingredients (excipients) such as binders, fillers, antioxidants, etc., and compressed into solid dosage forms that are subsequently swallowed. Most of the excipients used in immediate release tablets are water soluble, since this increases the rate at which the tablet dissolves. Lipophilic substances are often incorporated into sustained release dosage forms in order to delay the rate at which the tablet dissolves.

Tablets have also been used as a means of providing single serving consumer items such as laundry soap, dishwashing detergents, etc. Like pharmaceuticals, most of the ingredients found in soap are either water soluble or are amphilic (i.e. soluble in both water and oil) and thus will dissolve quickly.

Tablets have also been evaluated in the food industry as a serving form. However, food scientists have run into hurdles that have limited the potential commercial applicability of such tablets. For example, European Application Number 0 572 138 describes attempts to make tablets for subsequent reconstitution as sugar free soft drinks. The '138 application describes the dilemma confronting these scientists. Tablets made using compression pressures typical in the pharmaceutical industry are poorly soluble in cold water. Decreasing the pressure used in compression enhanced solubility but lead to brittle tablets that broke during shipping. The solution to this problem, as described by the '138 application, is two fold. First, lipophilic substances such as magnesium stearate were omitted from the formulation. Fat inhibited dissolution of the tablets. Secondly, carbonates, or other salts capable of generating carbon dioxide were incorporated into the formulation. The generation of carbon dioxide promoted the physical disintegration of the tablet thereby promoting the dissolution of the beverage mix in cold water.

Food scientists have also attempted to produce tablets out of powdered milks. As described by U.S. Pat. No. 3,241,975, less than optimal results have been obtained. As described by the '975 patent at column 1, lines 15–25, milk powders compressed into tablets have unacceptable solubility, even in hot water. The solution proposed by the inventors of the '975 patent is to alter the content of the powdered milk. Specifically they propose incorporating from 3 to 4% by weight of alkali metal phosphates or alkali citrates. These salts enhance the solubility of the casein and ultimately the dispersibility of the powdered milk. Further, supplemental lactose is incorporated into the powdered milk to enhance its dissolution rate. This supplemental lactose can comprise up to approximately 25% of the tablet. Even with these significant modifications, the tablets require hot water to exhibit suitable dispersibility.

German Patent 29908880 describes a milk tablet that is soluble in hot beverages. The tablet contains whey protein, sugar and optionally egg whites. Such a composition is essentially fat free. The German patent teaches that fat should be omitted from these milk tablets in order to be readily soluble in water.

European Patent Application 1 048 216 also addresses the production of milk tablets. At column 1, lines 1–15, the '216 application points out that most milk tablets are made from skim milk. Skim milk is essentially fat free, having a maximum fat content of 1.5% w/w. Skim milk is used since tablets made from whole milk tend to produce solutions suffering from phase separation. Further, dissolution times are substantially increased as the fat content increases. The '216 application discusses the preparation of high fat tablets, but only exemplifies their dissolution in water having a temperature of 700° C.

Thus, while the prior art shows that food products have been prepared in tablet form, it also shows that a number of problems exist. First, tablets are typically only used to produce low fat foods. Secondly, even these low fat food will not dissolve in cool water in an acceptable time frame.

Infant formula is high in fat. Approximately 50% of the calories contained in infant formula are derived from fat. In a powdered product, this constitutes approximately 25% of the formula, based on weight. Thus, one would consider infant formula a poor candidate for tablet development. The high fat content suggests such tablets would not dissolve quickly. Rapid dissolution is especially critical for infant formula. Infants communicate their hunger by crying. Caregivers and parents want dosage forms that dissolve instantly, so that the crying may be dissipated. For example, powdered infant formulas dissolves in cool water within 15 to 60 seconds. Any product having a reconstitution time beyond that would be considered unacceptable to most consumers.

SUMMARY OF THE INVENTION

In accordance with the present invention, it has been discovered that infant formula tablets will dissolve rapidly, despite the high fat content. The key to rapid dissolution is the rigorous control of compression pressures (i.e. the force used to compress the tablet). Excessive pressure leads to a film of fat being deposited on the exterior surface of the tablet. Tablets having this film of fat will not dissolve rapidly.

By contrast, tablets without this film dissolve within 60 seconds, with minor agitation. Dissolution times of 25 seconds have been routinely obtained. The exact pressure required to produce this result will vary with the type of tablet punch utilized and the composition of the infant formula. One skilled in the art can readily arrive at appropriate pressures with the teachings contained within this application.

The particular composition of the infant formula tablets is not critical to the invention. No unique ingredients are required to obtain the rapid dissolution times described above. Tablets have been manufactured containing soy proteins, bovine proteins, amino acids, hydrolyzed proteins, lactose free carbohydrate systems, etc.

DETAILED DESCRIPTION OF THE INVENTION

As used in this application, the following terms have the meanings defined below, unless otherwise specified. The plural and the singular should be treated as interchangeable:

a) the term "infant" refers to a child aged 1 year, or younger.

b) Any reference to a numerical range in this application should be construed as an express disclosure of every number specifically contained within that range and of every subset of numbers contained within that range. Further, this range should be construed as providing support for a claim directed to any number, or subset of numbers in that range. For example, a disclosure of 1–10 should be construed as supporting a range of 2–8, 3–7, 5, 6, 1–9, 3.64.6, 3.5–9.9, 1.1–9.9, etc.

c) Any reference to a dissolution test using the "manual method" refers to a test done in the following manner:

i) Testing—one tablet, of a predefined weight, is placed in an eight (8) ounce plastic formula bottle containing 60 cc of water, having a temperature of 30° C.±2°. The bottle is capped and then agitated for a predetermined test period. The test period can be 20, 30 or 60 seconds. The bottle is agitated using the wrist movement described immediately below.

At the conclusion of the test period, the cap is removed from the bottle and the contents are poured thru a US 80 mesh sieve. Any particulate matter retained on the screen is dried and weighed. The weight of the particulate matter should be less than, or equal to, 1% of the weight of the test tablet (i.e. at least 99% of the tablet must pass thru the 80 mesh sieve, based on weight). Foam is often visible on the screen. This foam is ignored.

ii) Agitation

A movement in which a eight (8) fluid ounce plastic infant formula bottle is placed in the left or right hand of the tester in the manner shown in FIG. 1. Whichever hand is predominant for the subject should be utilized.

The bottle should be gripped tightly by placing the fingers and thumbs around the sides of the bottle. The bottle is agitated in a movement involving both the wrist and elbow. The bottle is agitated vigorously for the predefined testing period. The exact motion is not critical. Examples of suitable movements are depicted in FIG. 1.

d) Any reference to a dissolution test using the "mechanical method" refers to a test done in the following manner.

i) Testing—one tablet, of a predefined weight, is placed in an eight (8) ounce plastic formula bottle containing 60 cc of water, having a temperature of 30° C.±2° C. The bottle is capped and then agitated as described below.

At the conclusion of the test period, the cap is removed from the bottle and the contents are poured thru US 80 mesh sieve. Any particulate matter retained on the screen is dried and weighed. The weight of the particulate matter should be less than, or equal to, 1% of the weight of the test tablet (i.e. at least 99% of the tablet must pass thru the 80 mesh sieve, based on weight). Foam is often visible on the screen. This foam is ignored.

ii) Agitation is provided by a horizontal reciprocating shaker having an amplitude of 0.4 foot. Such a device is available from DeFabco Inc., under the tradename the Ross Model # 1. DeFabco has an office at 3765 East Livingston Ave. Columbus, Ohio 43227.

A single 8 fluid ounce bottle is placed in the sample tray of the shaker and secured. The machine is turned on and agitated at the rate of 4 cycles per second. The testing is carried out for a predefined testing period, which is ninety (90) seconds, unless otherwise specified. FIG. 2 depicts the appearance of the shaker.

e) the term "infant formula" as used herein refers to a nutritional composition designed for children 1 year, or younger, which contains sufficient protein, carbohydrate, fat, vitamins, minerals, and electrolytes to serve as the sole source of the nutrition for these children, when provided in a sufficient quantity. Infant formula is currently commercially available as a ready-to-feed liquid, a concentrate that is diluted prior to consumption or a powder that is reconstituted prior to consumption. In addition to these forms, in this application, the term should be construed to include a tablet and any liquid infant formula resulting from the reconstitution of such tablets.

f) the term "tablet" refers to a solid of varying weight, size, and shape, which may be molded or compressed and which contains infant formula and which upon reconstitution may be used to provide nutrition to the infant.

Physical Appearance of Tablets

As noted above, the invention is the discovery of a new means of providing nutrition to an infant. The new means is a tablet. This tablet is reconstituted with water and the resulting solution is administered to an infant in the same manner as any other infant formula (i.e. via a nipple, with cereal, etc.). The physical appearance of these tablets is not unique. It typically is virtually indistinguishable from the dishwashing and laundry detergent tablets that are in widespread use today.

The size, shape, and weight of the tablet can vary widely and is not critical to the invention. Since the primary benefit of this invention is consumer convenience, the tablets will typically be formulated to provide a single serving of infant formula (i.e. on reconstitution will provide the amount of formula that an infant typically consumes in one feeding). The simplest manner of accomplishing this is to make one tablet equivalent to one scoop of powdered infant formula (i.e. comparable serving, dissolution instructions, etc.). Thus, one tablet will typically contain 8 to 9 grams of infant formula and will be dissolved in about 2 fluid ounces of water (60 milliliters). However, the invention is not limited to single serving tablets. If desired, larger tablets can be prepared which on reconstitution provide multiple feedings for an infant. Likewise multiple tablets can be dissolved at one time.

Composition of Tablets

The composition of the infant formula tablet is virtually indistinguishable from that of powdered infant formula. This is one of the key advantages of this invention. By preventing the occurrence of the fat film described above, the tablets do not require the presence of any substance whose sole purpose is to promote the dissolution of the tablet. Thus, the invention does not require the infant to be exposed to any substances that are not routinely fed to infants.

As noted above, infant formula contains protein, fat, carbohydrate, minerals, vitamins, and electrolytes. These components will be present in the tablets in amounts comparable to that included in powdered formula. On reconstitution, the tablets will produce a formula that is essentially identical to that obtained with either reconstituted powder or Ready-to-Feed formula. To further exemplify the invention, Table I provides guidance on typical quantities of protein, fat, and carbohydrate the tablets will contain (by weight and per 100 kcal). These are merely suggested amounts and depending upon the needs of the infant and the guidance of their pediatrician, the quantities can vary.

TABLE 1

Nutrient Guidelines*

| Nutrient (g) | Range | Per 100 kcal | By weight per 100 gm | Per liter (after reconstitution 20 cal/fl oz.) |
|---|---|---|---|---|
| Carbohydrate | Broadest | 8–16 | 30–90 | 54–108 |
| | Typical | 9–13 | 45–60 | 61–88 |
| Lipid | Broadest | 3–8 | 15–35 | 20–54 |
| | Typical | 4–6.6 | 20–30 | 27–45 |
| Protein | Broadest | 1–3.5 | 8–23 | 7–24 |
| | Typical | 1.2–3.4 | 12–20 | 9–23 |

*or as recommended by a pediatrician

The tablets will contain at least one source of carbohydrate. Carbohydrate is a major source of readily available energy that the infant needs for growth and that protects the infant from tissue catabolism. In human milk and most standard milk-based infant formulas, the carbohydrate is lactose.

The carbohydrates that may be used in the formula can vary widely. Examples of carbohydrates suitable for infants include hydrolyzed corn starch, maltodextrin, glucose polymers, sucrose, corn syrup, corn syrup solids, rice derived carbohydrate, glucose, fructose, lactose, high fructose corn syrup and indigestible oligosaccharides such as fructooligosaccharides (FOS). Any single carbohydrate listed above, or any combination thereof, as appropriate, may be utilized.

Lactose is typically the predominant carbohydrate in infant formula (like human formula). However, some infants are lactose intolerant. If desired, the carbohydrate source may be lactose free, or have reduced lactose content. Any carbohydrate that is considered suitable for consumption by human infants may be utilized to replace the lactose (i.e., a gram per gram replacement). Examples of suitable carbohydrates include hydrolyzed or intact, naturally and/or chemically modified starches sourced from corn, tapioca, rice or potato, in waxy or non-waxy forms. Other examples of low lactose carbohydrates include hydrolyzed cornstarch, maltodextrin, glucose polymers, sucrose, corn syrup, corn syrup solids, glucose, fructose, high fructose corn syrup and indigestible oligosaccharides, such as fructooligosaccharides (FOS). Any single carbohydrate listed above, or any combination thereof, as appropriate may be utilized. Other suitable carbohydrates will be readily apparent to those skilled in the art. Lactose free, and low lactose formula is described in detail in U.S. Patent Application Ser. No. 60/306,304, filed Jul. 18, 2001, the contents of which are hereby incorporated by reference.

Commercial sources for the carbohydrates listed above are readily available and known to one practicing the art. For example, corn syrup solids are available from Cerestar USA, Inc in Hammond, Ind. Glucose and rice based syrups are available from California Natural Products in Lathrop, Calif. Various corn syrups and high fructose corn syrups are available from Cargil in Minneapolis, Minn. Fructose is available from A. E. Staley in Decatur, Ill. Maltodextrin, glucose polymers, hydrolyzed corn starch are available from Cerestar USA, Inc., in Hammond, Ind. Sucrose is available from Domino Sugar Corp. in New York, N.Y. Lactose is available from Foremost in Baraboo, Wis. and indigestible oligosaccharides, such as FOS, are available from Golden Technologies Company of Golden, Colo.

The tablets will also include at least one source of amino nitrogen. The amino nitrogen source may be any protein or nitrogen source suitable for infant consumption. Such proteins are well known by those skilled in the art and can be readily selected when preparing such products. Examples of suitable protein sources include casein, whey, condensed skim milk, nonfat milk, soy, pea, rice, sesame seed, corn, hydrolyzed protein, free amino acids, and mixtures thereof.

Commercial protein sources are readily available and known to one practicing in the art. For example, caseinates, whey, hydrolyzed caseinates, hydrolyzed whey and milk proteins are available from New Zealand Milk Products of Santa Rosa, Calif. Soy and hydrolyzed soy proteins are available from Protein Technologies International of Saint Louis, Mo. Pea protein is available from Feinkost Ingredients Company of Lodi, Ohio. Rice protein is available from California Natural Products of Lathrop, Calif. Sesame seed protein is available from Dipasa USA, Inc., of Brownsville, Tex. Corn protein is available from EnerGenetics Inc. of Keokuk, Iowa. Additionally, mineral enriched proteins are available from New Zealand Milk Products of Santa Rosa, Calif. and Protein Technologies International of Saint Louis, Mo.

The tablets will also contain at least one source of lipid. Infants require lipids for optimal growth and development. Lipids provide energy, promote the absorption of fat-soluble vitamins, and provide the essential fatty acids that are required for normal growth and development. Any lipid that is suitable for consumption by a human infant may be utilized in the present invention. Examples of suitable lipids include coconut oil, soy oil, corn oil, olive oil, safflower oil, high oleic safflower oil, MCT oil (medium chain triglycerides), sunflower oil, high oleic sunflower oil, palm oil, palm olein, canola oil, and mixtures thereof.

A more preferred source of lipid is an admixture of high oleic safflower oil, soy oil, and coconut oil. Especially preferred lipids include a blend of vegetable oils containing about 38–50 weight % high oleic safflower oil (HOSO), about 26–40 weight % soy oil (SO) and about 22–36 weight % coconut oil (CO). These oils blend produce softer stools and enhance bone mineralization. They have been described in detail in U.S. patent application Ser. No. 60/286,140 filed Apr. 24, 2001, U.S. Pat. No. 6,136,858 and U.S. Pat. No. 6,248,784, the contents of each are hereby incorporated by reference.

In addition to these vegetable oils, the formula may also contain arachidonic acid, docosahexaenoic acid, and mixtures thereof. Such lipids have been reported to have beneficial effects in infants, including enhanced brain and vision development. U.S. Pat. No. 5,492,938 to Kyle et al. describes these effects in detail. Lipid sources of arachidonic acid and docosahexaenoic acid include, but are not limited to, marine oil, egg derived oils, fungal oil and algal oil. Marine oil is available from Mochida International of Tokyo, Japan. DHA and arachidonic acid are available from Martek Biosciences Corporation of Columbia, Md. Arachidonic acid is also available from Genzyme Corporation of Cambridge, Mass.

The infant formulas of this invention may optionally contain a stabilizer. Suitable stabilizers for use in infant nutritionals are well known to those skilled in the art. Suitable stabilizers include, but are not limited to, gum arabic, gum ghatti, gum karaya, gum tragacanth, agar, furcellaran, guar gum, gellan gum, locust bean gum, pectin, low methoxyl pectin, gelatin, microcrystalline cellulose, CMC (sodium carboxymethylcellulose), methylcellulose hydroxypropyl methyl cellulose, hydroxypropyl cellulose, DATEM (diacetyl tartaric acid esters of mono- and diglycerides), lecithin, mono-and diglycerols, and sodium steroyl lactate, dextran, carrageenans, and mixtures thereof. The amount of stabilizers utilized will vary depending upon the stabilizer(s) selected, the other ingredients present, and the stability and viscosity of the formula that is sought. Appropriate amounts can be determined by those of skill in the art based on the particular characteristics (e.g., viscosity, shelf life, acceptable sedimentation rates, etc.) being sought in the formula.

In addition to enhancing the stability of formula, gums may be included in order to raise the viscosity of the formula. Elevated viscosities have been shown to reduce the occurrence of spit-up in some infants. If desired, gums can be incorporated into the tablets so that the reconstituted infant formula will have viscosities in the range of 2 centipoise to 60 centipoise as measured by a Brooksfield viscometer at neutral pH's under standard conditions. Under acidic conditions, viscosities can approach 500 centipoise. Examples of suitable gums include gum arabic, gum ghatti, gum karaya, gum tragacanth, agar, furcellaran, guar gum, gellan gum, and locust bean gum. Alternatively, rice starch can be used to elevate viscosities. Formula for reducing infant spit-up is described in U.S. Pat. No. 6,099,871, filed May 3, 1996, the contents of which are incorporated by reference.

The tablets of this invention will also contain vitamins and minerals. Typically, one tablet will supply from 5 to 100% of the nutritional requirements specified by the Infant formula Act, infra or other relevant governmental guidelines. The formula preferably includes, but is not limited to, the following vitamins and minerals: phosphorus, sodium, chloride, magnesium, manganese, iron, copper, zinc, selenium, iodine, and Vitamins A, E, C, D, K and the B complex. Further nutritional guidelines for infant formulas can be found in the Infant Formula Act, 21 U.S.C. section 350(a). The nutritional guidelines found in the Infant Formula Act continue to be refined as further research concerning infant nutritional requirements is completed. This invention is intended to encompass formulas containing vitamins and minerals that may not currently be listed in the Act. (FIG. 3 outlines current requirements.)

In one embodiment, the invention is directed to an infant formula in tablet form comprising:
a) a source of protein, present in the amount of 10 to 20 w/w %;
b) a source of carbohydrate, present in the amount of 40 to 70 w/w %;
c) a source of fat, present in the amount of at least 20 w/w %;
d) sufficient vitamins and minerals to supply at least 10% of the requirements specified by the Infants Formula Act (IFA), and;
e) the tablet dissolves within 60 seconds when tested according to the manual protocol.

Other embodiments of this invention are directed to the use of the reconstituted tablet described immediately above to feed an infant. The invention is also directed to a container, suitable for retail sale, containing at least one such tablet and bearing a label advising that upon reconstitution, the tablet may be used as an infant formula.

In a further embodiment, the invention is directed to an infant formula tablet comprising, based on a 100 kcal basis:
a) about 8 to about 16 grams of a source of carbohydrate,
b) about 3 to about 8 grams of a source of fat,
c) about 1.0 to about 3.5 grams of a source of protein, and;
d) the tablet dissolves within 60 seconds when tested according to the manual protocol.

In one embodiment, the invention is directed to an infant formula in tablet form comprising:

a) a source of protein, present in the amount of 10 to 20 w/w %;
b) a source of carbohydrate, present in the amount of 40 to 70 w/w %;
c) a source of fat, present in the amount of at least 20 w/w %; and;
d) the tablet dissolves within 90 seconds when tested according to the mechanical protocol.

Other embodiments of this invention are directed to the use of the reconstituted tablet described immediately above to feed an infant. The invention is also directed to a container, suitable for retail sale, containing at least one such tablet and bearing a label advising that upon reconstitution, the tablet may be used as an infant formula.

In a further embodiment, the invention is directed to an infant formula tablet comprising, based on a 100 kcal basis:
a) about 8 to about 16 grams of a source of carbohydrate,
b) about 3 to about 8 grams of a source of fat
c) about 1.0 to about 3.5 grams of a source of protein, and;
d) the tablet dissolves within 90 seconds when tested according to the mechanical protocol.

Other embodiments of this invention are directed to the use of the reconstituted tablet described immediately above to feed an infant. The invention is also directed to a container, suitable for retail sale, containing at least one such tablet and bearing a label advising that upon reconstitution, the tablet may be used as an infant formula.

Use of Tablets in Feeding an Infant

As noted above, infant formula is currently commercially available in three different forms. One form is known as Ready-to-Feed (RTF) and as its name implies, the formula is fed directly to the infant as supplied by the manufacturer. RTF formula typically has a caloric density of 22 to 24 calories per fluid ounce for pre-term infants and 20 to 22 calories per fluid ounce for term infants. Infant formula is also available as a powder. This powder is reconstituted with tap water prior to administration to the infant. The quantity of powder required to produce a volume suitable for one feeding can vary, but generally ranges from about 8 to 9 grams. This volume of powder is reconstituted with about 55 to 65 milliliters of tap water to produce the nutrient densities described for RTF.

The infant formula tablets of this invention are reconstituted in a manner similar to that described for powdered infant formula. One tablet will typically contain from 8 to 9 grams of infant formula. One tablet is then reconstituted with sufficient water to produce the caloric densities outlined above. Typically, one tablet will be dissolved in approximately 55 to 65 cc of tap water and more typically about 60 cc of tap water.

Most infants consume formula via a nipple. This nipple has an aperture with a diameter ranging from 150 to 400 microns. Liquid infant formula often has solid particles suspended within it. These solid particles can be minerals, gums, lipids, etc.

It is important that these suspended particles be of a size of less than 250 microns. Typically these particles are smaller than 180 microns. Larger particles will clog the nipple leading to an interruption of feeding and typically a crying infant. Such disruptions in feeding are considered unacceptable in the market place.

Tablets coated with fat suffer from a further disadvantage beyond delayed dissolution times. The reconstituted formula produced from such tablets typically contains significant quantities of particulate matter having a size greater than 250 microns. Particles of this size will dog any feeding nipple in the manner described above.

Method of Manufacture

The starting material for the infant formula tablets is typically powdered infant formula. Methods for producing powdered infant formula are well known to those skilled in the art. The reader's attention is directed to U.S. Pat. No. 6,099,871 which discloses one method for producing such powders. U.S. Patent Application Ser. No. 60/306,304, filed Jul. 18, 2001, the contents of which are hereby incorporated by reference exemplifies the production of such powders.

As a general over view, powdered formula is prepared by the formation of a slurry from one or more solutions that contain water and one or more of the following: carbohydrates, proteins, lipids, stabilizers, vitamins and minerals. This slurry is emulsified, homogenized and cooled. The slurry will then be heated and dried to obtain a powder. The powder resulting from drying may be dry blended or agglomerated with further ingredients, if desired.

The simplest means to prepare the infant formula tablets is to compress commercially available powdered infant formula into tablets as described below. Table II below list suitable alternatives and their manufacturers based upon formula type.

TABLE II

Suitable Powered Infant Formula

| Formula Type | Brand Name | Manufacturer* |
|---|---|---|
| Soy Protein | Isomil ® | Ross |
|  | Prosobee ® | MJ |
| Milk Protein | Similac ® | Ross |
|  | Enfamil ® | MJ |
| DHA Supplemented | Enfamil Lipil ® | MJ |
|  | Similac Advanced ® | Ross |
| Anti-reflux | Enfamil AR ® | MJ |
| Lactose Free | Similac LF ® | Ross |
| Hydrolysed Proteins | Alimentum ® | Ross |
|  | Nutraminogen ® | MJ |
| Free Amino Acids | Elecare ® | Ross |

*MJ Mead Johnson Company, Evansville, IN
Ross Products Division, Abbott Laboratories, Columbus, OH The powdered formula is converted into tablets using techniques that are analogous to those used in the pharmaceutical industry to produce tablets. The readers attention is directed to Remington's Pharmaceutical Sciences, Fifteenth Edition pages 1576–1598 (1975), the disclosure of which is hereby incorporated by reference, which provides an overview of such tablet production. Unlike most pharmaceutical tablets no granulation step is required. The powdered infant formula may be compressed directly into tablets.

As a general guideline, a predetermined quantity of the powder is placed in a steel cavity (die). An upper steel punch 'is lowered into the die' exerting pressure on the powder thereby forming the tablet. The pressure required to form the tablet can vary widely depending upon the die/punch configuration utilized. However, as a general guideline a pressure in the range of about 400 to 1500 psi (pounds per square inch) will be utilized. Examples of suitable tablet die/punch combos include oval, concave, round, etc. However as noted above, excess pressure must be avoided in the punching. Excess pressure produces a film of fat on the tablet. Once this film forms, the tablets will not dissolve in the 20 to 60 seconds as exemplified below. Pressure in the ranges described above will produce tablets of sufficient hardness (friability) to withstand the typical rigors of packaging, distribution and handling normally associated with consumer goods.

The following Examples are being presented in order to further illustrate the invention. They should not be construed as limiting the invention in any manner.

EXAMPLE I

Preparation of Infant Tablets

Infant tablets were prepared individually using a manual Carver Press. The tablets were prepared from a powdered infant formula commercially available from the Ross Products Division of Abbott Laboratories. The formula is sold under the brand name, Isomil®, which is a formula whose sole protein source is soy protein isolate. The composition of the formula is described in the Ross Products Pediatric Nutritional Product Guide dated March 2001. Information may also be found at www.ross.com.

One scoop of formula (8.7 grams) was placed in a die having an internal diameter of 28.6 mm. An appropriate punch was used to produce a tablet. Initially a pressure of 400 pounds per square inch (psi) was used to produce a single tablet. This process was repeated and tablets were produced individually at pressures of 500 psi and 600 psi.

EXAMPLE II

Tablet Dissolution

The time required to dissolve the tablets produced in Example I was evaluated as described below. As an internal standard, a tablet was considered to have passed if it dissolved within 25 seconds, with minor manual agitation. The reconstituted infant formula was also poured thru a 80 mesh sieve to confirm its ability to pass thru a standard size infant nipple. A US 80 mesh sieve is a reliable tool for predicting whether a solution will pass thru a standard infant nipple. An 80 mesh sieve has pores having a diameter of 180 microns which is comparable to the aperture of nipples used to feed infants. The testing was conducted in the following manner.

One tablet, of a defined weight, was placed in an eight (8) ounce plastic formula bottle containing 60 cc of water, having a temperature of 30° C.±2° C. The bottle was capped and then agitated for a predetermined test period. The test period was 25 seconds.

At the conclusion of the test period, the cap was removed from the bottle and the contents were poured thru us 80 mesh sieve. The sieve was visually examined for undissolved particulate matter. If particulate matter was visible on the screen, then the tablet was determined to have failed the test. Foam was typically visible on the screen. This foam was ignored.

The following results were obtained. The tablets produced at 400 and 500 psi passed. The reconstituted infant formula passed thru the screen with no residue. This means that it would also pass thru an infant nipple without clogging. The tablet produced with 600 psi failed. It left particles greater than 180 microns on the screen. Particles of this size would clog a nipple and lead to an interruption of feeding.

EXAMPLE III

Tablet Friability (Breaking Strength)

The hardness of the tablets (i.e. breaking strength) produced in Example I was determined as described below. Tablet hardness is relevant because it correlates with tablet dissolution times.

Tablet breaking strength was measured with an Instron 5000 utilizing Merlin software. This test measures the amount of force required to break a tablet with a probe having a defined surface area. The test was carried out on three (3) tablets and the results were averaged. Results are reported as pounds per square inch.

The testing was carried out in the following manner. One tablet was placed in a receptacle positioned directly under the probe. The probe was lowered slowly until it made contact with the tablet. The distance the probe traveled and the resistance required to break the tablet was recorded in an S-shaped curve with the peak corresponding to the force used to break the tablet (reported in pounds per square inch, psi). The results are listed in Table III:

TABLE III

Tablet Friability

| | Compression Force | | | | |
|---|---|---|---|---|---|
| | 400 | | 550 | | 600 |
| Probe Size (in mm) | 3.15 | 4.7 | 3.15 | 4.7 | 3.15 |
| Avg. Breaking Strength (psi) | 1.42 | 6.09 | 2.58 | 8.98 | 3.55 |

EXAMPLE IV

Tablets were prepared from different powdered infant formulae using the procedures described in Example I. The composition of each these powders is described in Ross Products Guide, supra. The dissolution rate and hardness of the resulting tablets were determined using the protocols described in Examples II and ll. Breaking strength tests carried out with a 3.15 millimeter (mm) probe and labeled as A and those with a 4.7 mm are labeled as B. The results are documented in Table IV–VI below:

TABLE IV

Isomil ® Tablet

| | Tablet 1 | Tablet 2 | Tablet 3 |
|---|---|---|---|
| Compressing Strength (psi) | 400 | 550 | 600 |
| PASS Dissolution Test | Yes | Yes | No |
| Tablet Dimensions | | | |
| Diameter (mm) | 28.6 | 28.6 | N/A |
| Height (mm) | 19.35 | 18.8 | |
| Weight (gm) | 8.7 | 8.7 | |
| Avg. Force to Break/Probe (psi) | 1.42$^A$ | 2.58$^A$ | N/A |
| Avg. Force to Break/Probe (v) | 6.09$^B$ | 8.98$^B$ | N/A |

TABLE V

Similac ® Tablet

| | Tablet 1 | Tablet 2 | Tablet 3 |
|---|---|---|---|
| Compressing Strength (psi) | 400 | 900 | 1000 |
| PASS Dissolution Test | Yes | Yes | No |
| Tablet Dimensions | | | |
| Diameter (mm) | 28.4 | 28.6 | N/A |
| Height (mm) | 20.65 | 17.7 | |
| Weight (gm) | 8.4 | 8.4 | |
| Avg. Force to Break/Probe (psi) | 1.42$^A$ | 7.68$^A$ | N/A |
| Avg. Force to Break/Probe (v) | 3.94$^B$ | 16.7$^B$ | N/A |

TABLE VI

Isomil ® 2 Tablet

| | Tablet 1 | Tablet 2 | Tablet 3 |
|---|---|---|---|
| Compressing Strength (psi) | 400 | 500 | 600 |
| PASS Dissolution Test | Yes | Yes | No |
| Tablet Dimensions | | | |
| Diameter(mm) | 28.6 | 28.6 | N/A |
| Height (mm) | 19.05 | 18.2 | |
| Weight (gm) | 8.7 | 8.7 | |
| Avg. Force to Break/Probe (psi) | 1.7$^A$ | 2.9$^B$ | N/A |

EXAMPLE V

The inventors initial experiments focused on evaluating how quickly tablets would dissolve when shaken manually. Such experiments reflected how the product would be used by consumers in the real world. Experiments were also carried out with mechanical shakers to further explore product attributes.

The mechanical shaker chosen was a horizontal reciprocating shaker capable of shaking at an amplitude of 0.4 foot, at a frequency of 4 cycles per second, for a predetermined time period. The particular model used is available form DeFabco Inc. of Columbus Ohio and is known as the Ross Model#1 since it was co-designed previously with the assistance of Ross Labs of Columbus, Ohio.

The tablets were prepared in the same manner as those described in Example 1. Compression pressures were varied as described below. The tablets were prepared from powdered infant formula as described in Examples I–V above.

After the tablets had been prepared, an individual tablet was placed in an 8 fluid ounce plastic formula bottle containing 60 cc of water, having a temperature of 30° C.±2° C. The bottle was then placed in the sample tray of the shaker and secured. The bottle was then agitated at 4 cycles per second for a predetermined time period. The shaker automatically stops at the end of the test period. The contents were then poured thru an US 80 mesh sieve and examined for particulate matter in the manner described in Example I.

Tablets from the same batch were subject to both manual agitation and mechanical agitation. The following results were obtained:

TABLE VII

Isomil ®
Using Manual Shake

| | No. of Tablets | Fluid Ounce. | Time | Results* |
|---|---|---|---|---|
| 500 psi | 1 | 2 | 20 secs. | F |
| | 1 | 2 | 25 secs. | P |
| | 1 | 2 | 25 secs. | P |
| | 1 | 2 | 25 secs. | P |
| 600 psi | 1 | 2 | 25 secs. | F (marginal) |
| | 1 | 2 | 25 secs. | F (marginal) |

*P = pass
F = fail

TABLE VIII

Isomil ®
Using Mechanical Shake

| | No. of Tablets | Fluid Ounce | Time | Results* |
|---|---|---|---|---|
| 500 psi | 1 | 2 | 20 secs. | F |
| | 1 | 2 | 25 secs. | F |
| | 1 | 2 | 30 secs. | F |
| | 1 | 2 | 35 secs. | F |
| | 1 | 2 | 40 secs. | F |
| | 1 | 2 | 45 secs. | F |
| | 1 | 2 | 50 secs. | Marginal P |
| | 1 | 2 | 55 secs. | P |
| | 1 | 2 | 55 secs. | P |
| | 1 | 2 | 55 secs. | P |
| | 1 | 2 | 55 secs. | P |
| 600 psi | 1 | 2 | 55 secs. | F (marginal) |
| | 1 | 2 | 55 secs. | F (marginal) |
| | 1 | 2 | 55 secs. | F (marginal) |

*P = pass
F = fail

TABLE IX

Isomil ® 2
Using Manual Shake

| | No. of Tablets | Fluid Ounces | Time | Result* |
|---|---|---|---|---|
| 500 psi | 1 | 2 | 25 secs. | P |
| | 1 | 2 | 25 secs. | P |
| | 1 | 2 | 25 secs. | F (marginal) |
| | 1 | 2 | 25 secs. | P |
| | 1 | 2 | 25 secs. | P |
| 600 psi | 1 | 2 | 25 secs. | F |
| | 1 | 2 | 25 secs. | F |

*P = pass
F = fail

TABLE X

Isomil ® 2
Using Mechanical Shake

| | No. of Tablets | Fluid Ounces | Time | Result* |
|---|---|---|---|---|
| 500 psi | 1 | 2 | 55 secs. | F |
| | 1 | 2 | 55 secs. | F |
| | 1 | 2 | 60 secs. | F |

TABLE X-continued

Isomil ® 2
Using Mechanical Shake

| | No. of Tablets | Fluid Ounces | Time | Result* |
|---|---|---|---|---|
| | 1 | 2 | 70 secs. | F |
| | 1 | 2 | 90 secs. | F |
| 450 psi | 1 | 2 | 55 secs. | P |
| | 1 | 2 | 55 secs. | P |
| | 1 | 2 | 55 secs. | P |
| | 1 | 2 | 55 secs. | P |

*P = pass
F = fail

TABLE XI

Similac ®
Using Manual Shake

| psi | No. of Tablets | Fluid ounces | Time | Results* |
|---|---|---|---|---|
| 700 | 1 | 2 | 20 secs. | P |
| 800 | 1 | 2 | 20 secs. | P |
| 900 | 1 | 2 | 20 secs. | F (marginal) |
| 900 | 1 | 2 | 25 secs. | P |
| | 1 | 2 | 25 secs. | P |
| | 1 | 2 | 25 secs. | P |
| 1000 | 1 | 2 | 25 secs. | Marginal Failure |
| | 1 | 2 | 25 secs. | Marginal Failure |
| | 1 | 2 | 25 secs. | Marginal Failure |

*P = pass
F = failure

TABLE XII

Similac ®
Using Mechanical Shake

| | No. of Tablets | Fluid Ounces | Time | Results* |
|---|---|---|---|---|
| 900 psi | 1 | 2 | 25 secs. | F |
| | 1 | 2 | 30 secs. | F |
| | 1 | 2 | 35 secs. | Marginal Failure |
| | 1 | 2 | 40 secs. | P |
| | 1 | 2 | 40 secs. | P |
| | 1 | 2 | 40 secs. | P |
| | 1 | 2 | 40 secs. | P |
| | 1 | 2 | 40 secs. | P |

*P = pass
F = fail

TABLE XIII

Similac ® 2
Using Manual Shake

| | No. of Tablets | Fluid Ounces | Time | Results* |
|---|---|---|---|---|
| 900 psi | 1 | 2 | 25 secs. | Marginal F |
| | 1 | 2 | 25 secs. | Marginal F |
| | 1 | 2 | 30 secs. | Marginal P |
| | 1 | 2 | 30 secs. | Marginal P |
| 800 psi | 1 | 2 | 25 secs. | P |
| | 1 | 2 | 25 secs. | P |
| | 1 | 2 | 25 secs. | P |

*P = pass
F = fail

TABLE XIV

Similac ® 2
Using Mechanical Shake

| | No. of Tablets | Fluid Ounces | Time | Results* |
|---|---|---|---|---|
| 800 psi | 1 | 2 | 40 secs. | P |
| | 1 | 2 | 40 secs. | P |
| | 1 | 2 | 40 secs. | P |
| | 1 | 2 | 40 secs. | P |

*P = pass
F = fail

As shown above, the tablets dissolved quicker when agitated manually. It was determined that a time period of from 40 to 55 seconds was typically required to obtain dissolution of the tablets with a mechanical shaker. If the excess pressure had been used and the tablets would not dissolve manually, comparable results were obtained with the mechanical method.

The criterion used in these tests are stricter than those specified in the claims and on page 4. The inventors were attempting to obtain 100% dissolution of the tablets. If total dissolution was not obtained, the experiment was reported as a failure. It should be noted that 1% of the tablet may not dissolve when using the protocols described on page 4 of the specification.

We claim:

1. An infant formula in tablet form comprising:
   a) a source of protein, present in the amount of 10 to 20 w/w %;
   b) a source of carbohydrate, present in the amount of 40 to 70 w/w %; and
   c) a source of fat present in the amount of at least 20 w/w %;
   wherein the infant formula is a tablet formed under a pressure selected from within a range of from about 400 psi to about 1500 psi, and wherein the pressure is selected so that a film of fat does not form on the exterior tablet surface, and wherein the resulting infant formula tablet dissolves within 60 seconds in accordance with a manual dissolution test.

2. The formula according to claim 1 in which said fat is present in the quantity of at least 25 w/w %.

3. The formula according to claim 1 in which said protein is present in the quantity of 11 to 16 w/w %.

4. The formula according to claim 1 in which said carbohydrate is present in the quantity of about 50 to 60 w/w %.

5. The formula according to claim 1 in which said protein is selected from the group consisting of intact protein, hydrolyzed protein and amino acids.

6. The formula according to claim 1 wherein the protein comprises intact protein selected from the group consisting of soy based protein, milk based protein, casein protein, whey protein, rice protein, and pea protein.

7. The formula according to claim 1 wherein the protein comprises hydrolyzed protein selected from the group consisting of soy protein hydrolysate, casein protein hydrolysate, whey protein hydrolysate, and rice protein hydrolysate.

8. The formula according to claim 1 wherein the protein comprises free amino acids selected from the group consisting of L-tryptophan, L-tyrosine, L-cystine, L-taurine, L-methionine, L-arginine, and L-carnitine.

9. The formula according to claim 1 wherein the carbohydrate is selected from the group consisting of hydrolyzed, intact, natural and chemically modified starches sourced from corn, tapioca, rice or potato in waxy or non waxy forms; sugars such as glucose, fructose, lactose, sucrose, maltose, high fructose corn syrup; and mixtures thereof.

10. The formula according to claim 1 wherein the fat is selected from the group consisting of coconut oil, soy oil, corn oil, olive oil, safflower oil, high oleic safflower oil, medium chain triglyceride oil, sunflower oil, high oleic sunflower oil, palm oil, palm olein, canola oil, arachidonic acid and docosahexaneoic acid.

11. A method for providing nutrition to an infant comprising dissolving the tablet of claim 1 and feeding the resulting formula to an infant in need thereof.

12. An infant formula in tablet form comprising, based on a 100 kcal basis:
   a) about 8 to about 16 grams of a source of carbohydrate,
   b) about 3 to about 6 grams of a source of fat, and
   c) about 1.8 to about 3.3 grams of a source of protein,
   wherein the infant formula is a tablet formed under a pressure selected from within a range of from about 400 psi to about 1500 psi, and wherein the pressure is selected so that a film of fat does not form on the exterior tablet surface, and wherein the resulting infant formula tablet dissolves within 60 seconds in accordance with a mechanical dissolution.

* * * * *